United States Patent [19]

Zusi et al.

[11] Patent Number: 4,731,382

[45] Date of Patent: Mar. 15, 1988

[54] LIPOXYGENASE INHIBITORY PHENYLALKANOHYDROXAMIC ACIDS

[75] Inventors: Fred C. Zusi; Suresh A. Marathe, both of Tonawanda; Kenneth M. Tramposch, Williamsville, all of N.Y.

[73] Assignee: Bristol-Myers Company, New York, N.Y.

[21] Appl. No.: 947,334

[22] Filed: Dec. 29, 1986

[51] Int. Cl.$^4$ .................... C07C 87/10; A61K 31/185
[52] U.S. Cl. .......................... 514/575; 260/500.5 H
[58] Field of Search ................ 260/500.5 H; 514/575

[56] References Cited

U.S. PATENT DOCUMENTS

| 2,397,500 | 4/1946 | Rousult et al. | 260/500.5 H |
| 3,328,138 | 6/1967 | Malec et al. | 44/71 |
| 3,479,396 | 11/1969 | Buu-Hoi et al. | 260/500.5 H |
| 4,188,338 | 2/1980 | Bruins et al. | 260/500.5 H |
| 4,564,476 | 1/1986 | Ho | 260/404 |
| 4,604,407 | 8/1986 | Haslanger et al. | 514/575 |
| 4,605,669 | 8/1986 | Summers, Jr. | 260/500.5 H |
| 4,608,390 | 8/1986 | Summers, Jr. | 260/500.5 H |

FOREIGN PATENT DOCUMENTS 161939 11/1985 European Pat. Off. .
196674 10/1986 European Pat. Off. .
199151 10/1986 European Pat. Off. .

OTHER PUBLICATIONS

J. Am. Chem. Soc., 1984, 106, pp. 1503-1504.
Chem. Pharm. Bull. 31, (8) pp. 2810-2819 (1983).
Chem. Abstract Japanese Kokai, 59/46244.

Primary Examiner—J. E. Evans
Attorney, Agent, or Firm—David M. Morse

[57] ABSTRACT

Compounds of the formula

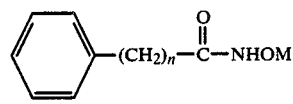

I where n=6-11 and M is hydrogen or a pharmaceutically acceptable cation are potent inhibitors of 5-lipoxygenase.

20 Claims, No Drawings

LIPOXYGENASE INHIBITORY PHENYLALKANOHYDROXAMIC ACIDS

BACKGROUND OF THE INVENTION

1. Field of the Invention

The present invention relates to novel hydroxamic acid compounds which inhibit the enzyme, 5-lipoxygenase. The metabolism of arachidonic acid via 5-lipoxygenase gives rise to products implicated as mediators in certain inflammatory and allergic disease states. Inhibition of 5-lipoxygenase blocks the production of such mediators and alleviates the inflammatory and allergic conditions resulting therefrom.

2. Description of the Prior Art

The literature reveals a large number of hydroxamic acid derivatives, some of which possess lipoxygenase-inhibitory activity and/or pharmaceutical activities associated with inhibition of lipoxygenase enzymes.

At the Gordon Conference in Medicinal Chemistry held July 28-Aug. 1, 1986 in New London, N.H. a handout was distributed disclosing, inter alia, compounds of the formula

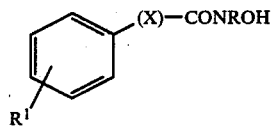

as 5-lipoxygenase inhibitors. Biological data was provided for phenylalkylhydroxamic acids of the formula

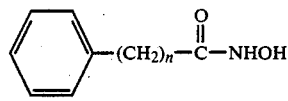

where n=0, 1, 2 or 3, but no mention was made of compounds with longer alkyl groups such as the n=6-11 compounds of the present invention. These compounds were also disclosed at the 1986 Fall American Chemical Society Meeting Sept. 8, 1986–Sept. 12, 1986) in Anaheim, Calif.

Japanese Kokai No. 59/46244 in the name of Nissan Chemical Co. discloses hydroxamic acid derivatives of the formula

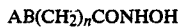

where
A is $RX_m$ in which
R is phenyl, pyrrolyl, thienyl, imidazolyl or thiazolyl;
X is halogen, lower alkyl, lower alkoxy or nitro;
m is 0, 1, or 2;
the X substituents may be the same or different;
B is —CHOH—, —CH$_2$—, —O— or ;13 CO— and n=2-10 as anti-protozoal agents. The only compound disclosed where B is —CH$_2$— and A is phenyl is the compound of the formula

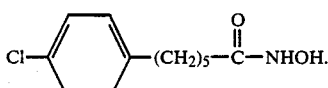

There is no mention of lipoxygenase-inhibitory activity. Applicants have tested the corresponding unsubstituted phenyl compound of the formula

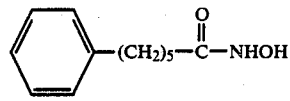

in the 5-lipoxygenase inhibition test reported in the text below and have found such compound to have an IC$_{50}$ ($\mu$M) of >100 compared with an IC$_{50}$ value of 20.9 for the compound of the present invention having the formula

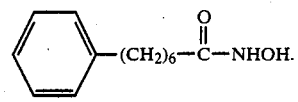

European Patent Application No. 161,939 discloses substituted benzohydroxamic acids of the formula

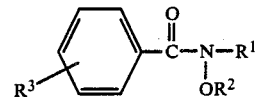

where, inter alia, R$^1$ and R$^2$ may be hydrogen, as lipoxygenase inhibitors. They may be distinguished from the present compounds by the lack of a carbon chain between the phenyl ring and the hydroxamic function.

K. Tanaka, et al. in *Chem. Pharm. Bull.* 31: 2810–2819, 1983, disclose some substituted phenylpropionohydroxamic acids of the type

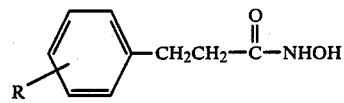

which are reported to have antiinflammatory activity. These compounds are distinguished from the present compounds by having a shorter alkyl chain length which has been found to be inappropriate for good activity.

U.S. Pat. No. 4,564,476 discloses a series of lipoxygenase inhibitors of the general formula

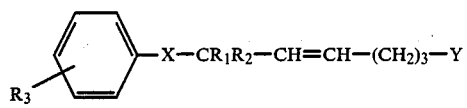

in which, inter alia, R$_1$, R$_2$ and R$_3$ may by hydrogen, X is O or CH=CH and Y may be —CONHOH. The compounds may be distinguished from the present compounds in that (1) they must have at least one double bond plus one heteroatom or at least two double bonds in the sidechain and (2) there is no specific disclosure of compounds having the hydroxamic acid group.

E. J. Corey et al. in *J. Amer. Chem. Soc.* 106: 1503–1504, 1984, discloses the compound

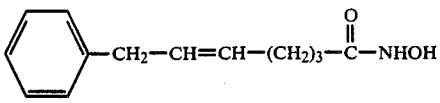

as a lipoxygenase inhibitor. This compound may be distinguished from the present compounds by the presence of the double bond in the sidechain.

U. S. Pat. No. 3,328,138 generically discloses hydroxamic acids of the formula

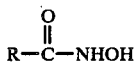

where, inter alia, R may be alkyl substituted by aryl, the entire radical having from 7-28 carbon atoms, as motor fuel additives.

U.S. Pat. No. 3,479,396 discloses compounds of the formula

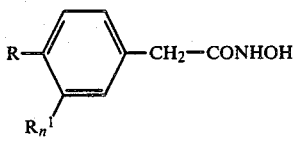

where R and $R^1$ can be alkyl, cycloalkyl, alkyloxy, alkenyloxy, cycloalkenyloxy, alkylthio, cycloalkyloxy, cycloalkylalkyloxy or arylalkyloxy; $R^1$ can also be hydrogen, and n is an integer of 0 to 2 as having antipyretic, antiinflammatory, antispasmodic and analgesic properties. These compounds have only one carbon atom in the alkyl chain.

U.S. Pat. No. 4,188,338 discloses, inter alia, ring-substituted compounds of the type

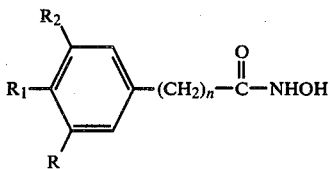

where R is alkoxy, alkenyloxy, alkyl or benzyloxy, $R_1$ and $R_2$ are H, alkoxy, alkenyloxy, benzyloxy or alkyl and n=2-3 as having inhibitory activity against blood platelet aggregation. In the specification (column 1, lines 20-60) it is stated that as the chain length increases the antiinflammatory activity decreases and that the disclosed compounds specifically have no antiinflammatory activity (column 2, lines 43-50). This leads away from expecting potent antiinflammatory activity in compounds where n is ≧2 such as those of the present invention where n=6-11.

Japanese Pat. No. 61/33,115 discloses a series of naphthloxyalkyl hydroxamic acids of the formula

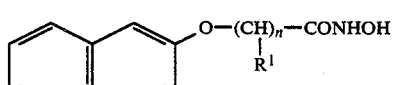

$R^1$ = H when n = 1-10 as antiinflammatory agents. These compounds may be distinguished from the present compounds by the presence of the oxygen atom in the sidechain and a naphthyl instead of a phenyl group.

U.S. Pat. No. 4,579,866 (equivalent to Japanese 61/00054) discloses 5-lipoxygenase inhibitors of the formula

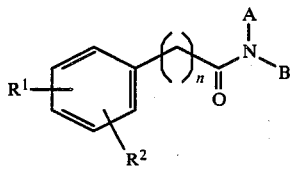

where
$R^1$ and $R^2$ are independently H, OH, lower alkyl, lower alkoxy, aryloxy, heteroaryloxy, heteroaryl lower alkoxy, aryl, heteroaryl, aryl-lower alkyl, aryl-lower alkoxy, halogenated aryl-lower alkoxy, lower alkenyl, lower alkynyl, lower alkenyloxy, lower alkynyloxy, halogen or trifluoromethyl;
A is H, aryl, lower alkyl, aryl-lower alkyl or heteroaryl; and
B is

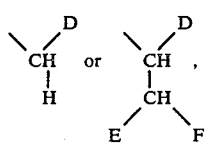

n=0-6,
wherein D is H, $CONR_3R_4$, $CO_2H$, $CO_2R_5$, $CH_2OH$ or $CH_2OR_6$,
wherein
$R_3$, $R_4$, $R_5$ and $R_6$ are independently H, lower alkyl, aryl, aryl-lower alkyl or heteroaryl;
E is H, OH, lower alkyl, aryl or heteroaryl; and
F is

in which G is the same as $R_1$ and $R_2$. The present compounds may be distinguished by the presence of a hydroxamic functional group which has been found necessary for good activity.

U.S. Pat. No. 4,608,390 discloses compounds of the formula

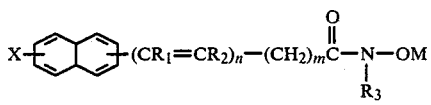

where
X is H, $C_1$-$C_{22}$ alkyl or alkenyl, or an electron-withdrawing group;
n is 0 or 1 and m is 0, 1, 2 or 3; but n and m are not 0 simultaneously;
$R_1$ and $R_2$ independently are H, $C_1$-$C_6$ alkyl, and electron-withdrawing group or $R_4$;
$R_3$ is H, $C_1$-$C_6$ alkyl or cycloalkyl, or $R_4$; and
$R_4$ at each occurrence, has the formula

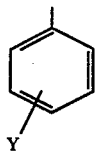

where Y is hydrogen or an electron-withdrawing group; and wherein M is a pharmaceutically acceptable cation, as lipoxygenase inhibitors. Among the compounds designated as Ex. Nos. 18 and 19 are those of the formula

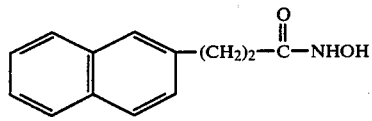

and

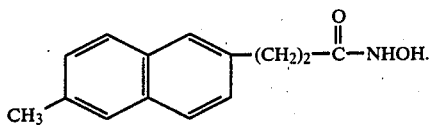

These compound may be distinguished from the present compounds by the presence of a naphthyl instead of a phenyl group and a shorter alkyl chain.

U.S. Pat. No. 4,605,669 discloses lipoxygenase-inhibiting naphthohydroxamic acids of the formula

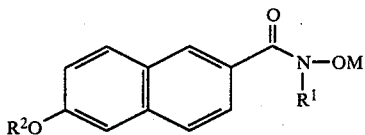

where $R^1$ is H or $C_1-C_6$ alkyl; $R^2$ is $C_1-C_{22}$ alkyl, cycloalkyl, aralkyl or alkenyl; and M is a pharmaceutically acceptable cation. These compounds have naphthyl instead of phenyl and have no alkyl chain.

European Patent Application 199,151 A2 discloses lipoxygenase-inhibiting compounds of the formula

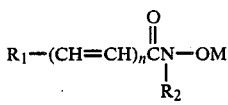

where $R_1$ is trinuclear aromatic or biaryl group; $R_2$ is hydrogen or $C_1-C_6$ alkyl or cycloalkyl; n is 0 or 1; and M is a pharmaceutically acceptable cation. Again, these compounds do not have a phenyl group in the sidechain and have either no alkyl chain or a double bond in the chain.

European Patent Application No. 196,674 discloses lipoxygenase-inhibiting hydroxamate compounds of the formula

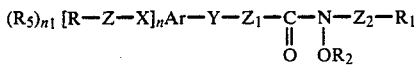

where
$R_2$ is H, lower alkyl, formyl or $C_2-C_{10}$ alkanoyl;

R and $R_1$ are ach independently hydrogen, lower cycloalkyl, fused cycloalkyl or lower alkyl-substituted fused cycloalkyl, lower alkyl, phenyl, naphthyl or a nitrogen, oxygen or sulfur heterocyclic ring or heterocyclic-lower alkyl;

Z, $Z_1$ and $Z_2$ are each a chemical bond or an alkylene chain or a mono- or disubstituted alkylene chain containing up to 6 carbon atoms in the principal chain and up to a total of about 10 carbon atoms, a lower cycloalkyl, a nitrogen, oxygen or sulfur heterocyclic ring or heterocyclic lower alkyl, or a mono- or di-substituted lower cycloalkyl or heterocyclic lower alkyl;

X and Y are each independently O, S, $CR_3$, $R_4$ or a chemical bond;

$R_3$ and $R_4$ are each independently H or lower alkyl; each $R_5$ is H, aryl, lower alkarayl, formyl, nitro, cyano, amino, lower aminoalkyl, lower alkylamino, lower aralkylamino, halo, trihalo alkyl, carbamoyl or aroyl;

n is an integer from 0-2; and $n_1$ is an integer from 1-2. By judicious selection of the appropriate variables, one can obtain compounds of the formula

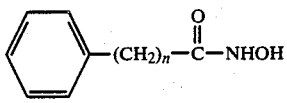

where n can be up to seven carbons in length. However, $Z_1$ is preferably only up to three carbon atoms in length, thus making the preferred compounds of the above formula those with $n \leq 4$. The lack of any specific disclosure of longer chain compounds together with the disclosed preference for $n \leq 4$ teaches away from applicants' compounds having n=6-11.

Despite the disclosure in the literature of various 5-lipoxygenase-inhibiting compounds as illustrated above, there is a need for more potent inhibitors of this enzyme.

SUMMARY OF THE INVENTION

Phenylalkyl hydroxamic acid compounds of the formula

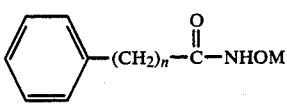

I wherein n is an integer from 6 to 11 and M is hydrogen or a pharmaceutically acceptable cation are novel and potent inhibitors of 5-lipoxygenase and are thus useful in the treatment of certain inflammatory and allegic disorders in mammals, e.g. humans, such as asthma and other chronic obstructive pulmonary diseases, arthritis, psoriasis, atopic eczema and chronic colitis.

DETAILED DISCLOSURE

The novel lipoxygenase-inhibiting compounds of the present invention are of the formula

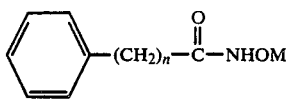

I wherein n is an integer from 6 to 11, more preferably 7-9 and most preferably 8, and M is hydrogen or a pharmaceutically acceptable cation.

The hydroxamic acid compounds of Formula I where M is hydrogen may be converted by methods known per se into pharmaceutically acceptable salts by reacting the acid with a suitable base providing a nontoxic cation. Suitable nontoxic cations may be based on the alkali metals and alkaline earth metals, e.g. sodium, potassium, lithium, calcium, magnesium, and the like. Also suitable are nontoxic ammonium, quaternary ammonium and amine cations such as ammonium, tetramethylammonium, tetraethylammonium, methylamino, dimethylamino, trimethylamino, triethylamino and ethylamino.

The compounds of Formula I may be prepared by known methods for the synthesis of hydroxamic acids.

One useful method is to start with commercially available phenylalkyl carboxylic acids of the formula

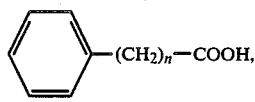

transform them to an activated acid derivative such as an ester, acid halide or anhydride and then condense the activated acid with hydroxylamine in the presence of base. This procedure may be illustrated by the following reaction scheme:

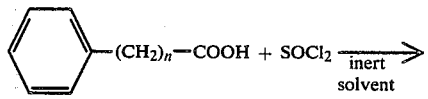

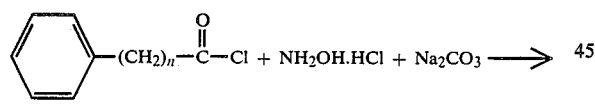

II

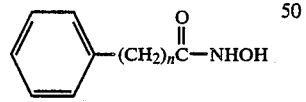

More particularly, the carboxylic acid is preferably converted to an acyl chloride by treatment with thionyl chloride in an inert solvent such as methylene chloride. The acid chloride is then condensed with hydroxylamine hydrochloride in the presence of a base such as Na$_2$CO$_3$ or triethylamine in an inert solvent such as methylene chloride.

In certain cases where the starting acids are not readily available, they may also be prepared by methods known in the art. For example, an α,ω-dicarboxylic acid may be condensed to a cyclic anhydride using a dehydrating agent such as acetic anhydride, and the cyclic anhydride may be condensed with benzene in the presence of a Friedel-Crafts catalyst such as aluminum trichloride to give an ω-phenylketoacid. The ketoacid may then be reduced to the desired phenylalkyl carboxylic acid by reducing agents such as zinc amalgam. This process is illustrated in the following reaction scheme:

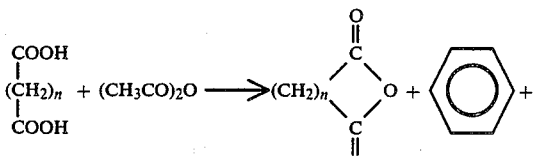

III

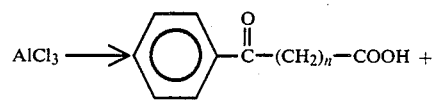

IV

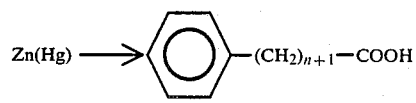

In still other cases, especially long-chain dicarboxylic acids where the cyclic anhydride III is not readily formed, the desired intermediate ketoacid IV can be obtained by protecting the diacid as the diester, deprotecting only one end of the diester by limited hydrolysis, converting the deprotected acid to an acyl halide, condensing the acyl halide with benzene to give a protected phenylketoester, and hydrolyzing the ester by known methods. This procedure is illustrated by the following scheme:

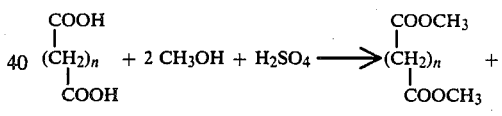

V

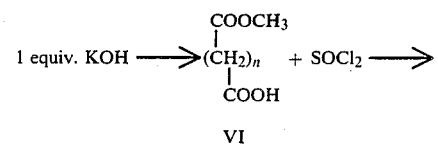

VI

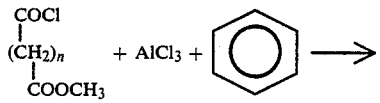

VII

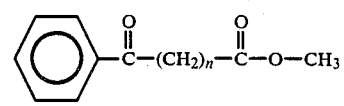

VII

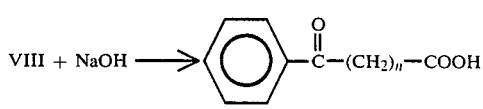

IV

These ketoesters IV may then be carried forward as described above.

Compounds of Formula I have been found to have potent inhibitory activity against 5-lipoxygenase enzyme when tested in a mixed neutrophil/platelet system. This test is a measure of the inhibition of the synthesis of lipoxygenase products generated by human neutrophils and platelets. The protocol is similar to that described in the article "Comparative Effects of Indomethacin, Acetylenic Acids, 15-HETE, NDGA and BW755C on the Metabolism of Arachidonic Acid in Human Leukocytes and Platelets", H. Solari, P. Braquet and P. Borgeat, *Prost. Leuk. Med.* 13, pp. 53-60, 1984.

Human neutrophils and platelets were obtained from the blood of normal volunteers. The blood was collected into tubes containing EDTA as an anticoagulant. The blood was centrifuged at 250×g for 15 minutes an the platelet rich plasma was removed. The cell fraction was mixed with an equal volume of 0.9% saline containing 10 mM dextrose and resuspended in Dulbecco's phosphate buffered saline (PBS) without $Mg^{++}$ and $Ca^{++}$ and was counted. The cell suspension was adjusted to give a leukocyte count of $2-3 \times 10^7$ cells/ml. The platelet contamination in these preparations was 0.1 to 0.5 platelets/leukocyte.

Test compounds were dissolved in ethanol and added to polypropylene tubes. To control tubes (drug-free) only ethanol was added. The ethanol was evaporated to dryness under a stream of argon and then 0.1 ml of the cell suspension ($2-3 \times 10^6$ cells) was added. This mixture was pre-incubated for 5 minutes at 37° and then the reaction was initiated by addition of $^3$H-arachidonic acid, calcium ionophore (A23187), and calcium ion. The final concentration of each component was: arachidonic acid, 10 uM; A23187, 1.25 mg/ml; calcium ion, 2 uM. After 5 minutes the incubations were stopped by addition of an equal volume of methanol. The tubes were spun at 11,000 g for 2 minutes to pellet the precipitated protein. The supernatant was analyzed by HPLC for 5-HETE. The formation of this product is indicative of 5-lipoxygenase activity. Test drugs were evaluated for their ability to inhibit 5-HETE formation.

Percent inhibition of varying concentrations of test drugs was determined in duplicate by comparing the peak quantitation in the presence and absence (control) of drug. The results in Table I report the $IC_{50}$ values. The $IC_{50}$ values were calculated from log-dose response curves of pooled data from at least two experiments by linear regression analysis. Table I also includes, for comparison purposes, $IC_{50}$ data of compounds of the indicated formula having n values of <6 and >11.

TABLE I

Inhibition of Human Leukocyte 5-LPO

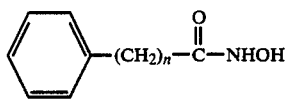

| Compound | n | $IC_{50}$ (μM) 5-LPO |
|---|---|---|
|  | 0 | >100 |

TABLE I-continued

Inhibition of Human Leukocyte 5-LPO

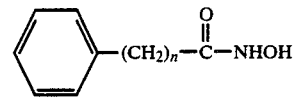

| Compound | n | $IC_{50}$ (μM) 5-LPO |
|---|---|---|
|  | 1 | >100 |
|  | 2 | >100 |
|  | 3 | >100 |
|  | 4 | >100 |
|  | 5 | >100 |
| 2a | 6 | 20.9 |
| 2b | 7 | 12.2 |
| 1 | 8 | 5.7 |
| 2c | 9 | 11.6 |
| 2d | 10 | 11 |
| 2e | 11 | 10.3 |
|  | 12 | >50 |
|  | 14 | >100 |

The compound of Formula I where n=8 was evaluated in the carrageenan sponge implantation model and found to have activity in this in vivo animal system predictive for inflammatory disease.

The carrageenan sponge implantation model is primarily used to measure the effect of antiinflammatory agents on cell infiltration. An acute inflammatory response is stimulated by the implantation of a small sponge beneath the skin of rats. The sponge normally contains an inflammatory stimulus such as carrageenan and produces a response which is characterized by infiltration of cells and accumulation of fluid. The number of cells in the exudate can be conveniently measured in the exudate fluid.

The compound of Example I was evaluated for its local effect on cell migration and mediator production in this model. For comparison, indomethacin and BW755C were also evaluated after local application. Polyester sponges were soaked in solutions of 0.5% carrageenan (in normal saline) which also contained 1% wt/vol of the test compound. The impregnated sponge was inserted through a small incision on the dorsal surface of a lightly anesthetized rat into a subcutaneous pocket formed by blunt dissection. The incision was then closed. The control treateament consisted of a sponge soaked in 0.5% carrageenan in normal saline. Animals were sacrificed 6 hours after sponge implantation. Sponges are dissected out and placed in heparinized saline. The number of infiltrating cells were determined using a coulter counter. The inflammatory mediators prostaglandin $E_2$, $LTB_4$ and $TxB_2$ in the exudate were determined by radioimmunoassay.

The results of the effect of Compound 1, indomethacin and BW755C on cell infiltration and mediator production is shown in Table II. Compound 1 dosed at 1% and 5% reduced cell infiltration by 36.1 and 96% respectively. In contrast indomethacin at 1% did not significantly reduce cell infiltration. BW755C dosed at 5% reduced cell infiltration by 79%. All of the treatments reduced the concentrations of mediators in the exudate.

TABLE II

| Treatment | Leukocyte No. cells/ml (× $10^{-6}$) | ng/ml Exudate | | |
|---|---|---|---|---|
|  |  | $PGE_2$ | $TXB_2$ | $LTB_4$ |
| Experiment 1 | | | | |

TABLE II-continued

| Treatment | Leukocyte No. cells/ml (× 10⁻⁶) | ng/ml Exudate | | |
|---|---|---|---|---|
| | | PGE$_2$ | TXB$_2$ | LTB$_4$ |
| Control (0.5% Carrageenan) | 10.8 ± 1.5 | 10.8 ± 3.7 | 3.6 ± 1.3 | 11.8 ± 4.1 |
| Compound 1 (0.5% Carrageenan plus 1% Compound 1) | 6.9 ± .7 | 5.7 ± 0.9 | 0.3 ± 0.1 | 2.1 ± 1.0 |
| Indomethacin (0.5% Carrageenan plus 1% Indomethacin) | 8.4 ± 1.7 | 1.9 ± 0.3 | <0.5 | 1.6 ± 0.5 |
| Experiment 2 | | | | |
| Control (0.5% Carrageenan) | 33.0 ± 3.8 | 137.6 ± 13.1 | 19.2 ± 1.9 | 5.5 ± 0.9 |
| Example (0.5% Carrageenan plus 5% Compound 1) | <1 | 21.3 ± 4.1 | 4.1 ± 0.9 | 2.4 ± 0.9 |
| BW755C (0.5% Carrageenan plus 5% BW755C) | 6.9 ± 1.7 | 3.0 ± 1.0 | 0.8 ± 0.3 | N.D. |

N.D. = not detected

These results indicate that the compounds of the present invention can reduce cellular infiltration and mediator production in an in vivo system. Since cell infiltration is a characteristic of many inflammatory conditions, the compounds of the present invention are useful in treating inflammatory disease.

In addition to providing the novel compounds of Formula I, the present invention provides a method of inhibiting 5-lipoxygenase activity in a mammal (human or lower animal host) in need of such treatment, which method comprises administering to said mammalian host an amount of a compound of Formula I effective to inhibit lipoxygenase activity in the host. The compounds may be administered orally, parenterally or topically in dosage unit formulation containing conventional pharmaceutically acceptable carriers.

Also provided is a method of preventing or treating inflammation in a mammalian host, which method comprises administering to a host in need of such treatment a therapeutically effective amount of a compound of Formula I. The compound may be administered orally, parenterally or topically.

The term "parenteral" as used herein includes intravenously, intramuscularly and subcutaneously. The term "topical" as used herein includes administration rectally and by inhalation spray as well as by the more common routes of the skin and the mucous membranes of the mouth and nose.

Total daily dose of the compounds of the invention administered to a host in single or divided dose may be in amounts of from about 0.001 to 2000 mg/kg body weight daily and more generally about 0.01 to 10 mg/kg/day. Dosage unit compositions may contain such amounts or such submultiples thereof as may be used to make up the daily dose. It will be understood, however, that the specific dose level for any particular patient will depend upon a variety of factors including the activity of the specific compound administered, the age, body weight, six, diet, time and route of administration, rates of absorption and excretion, combination with other drugs and the type and severity of disease being treated.

Also provided by the present invention are pharmaceutical compositions in unit dosage form for the inhibition of 5-lipoxygenase activity in a mammalian host in need of such treatment, comprising an effective amount of a compound of Formula I and one or more pharmaceutically acceptable carriers.

Pharmaceutical compostions in unit dosage form for the treatment or prevention of inflammation in mammals are also provided, said compositions comprising a therapeutically effective amount of a compound of Formula I and one or more pharmaceutically acceptable carriers.

A variety of materials can be used as carriers in the pharmaceutical compositions of the present invention. Injectable preparations, such as sterile injectable aqueous or oleaginous solutions, suspensions or emulsions, may be formulated according to known methods, using suitable dispersing or wetting agents and suspending agents, as needed. The sterile injectable preparation may employ a nontoxic parenterally acceptable diluent or solvent as, for example, sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile fixed oils are conventionally employed as solvents or suspending media. For this purpose any bland fixed oil may be used including synthetic mono-, di- or triglycerides. Fatty acids such as oleic acid can also be used in the preparation of injectable compositions.

Suppositories for rectal administration can be prepared by mixing the drug with suitable nonirritating excipients such as cocoa butter and polyethylene glycols which are solid at ordinary temperatures but liquid at body temperature and which therefore melt in the rectum and release the drug.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. In the case of capsules, tablets and pills, the dosage forms may also contain buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art such as water and alcohol. Such compositions may also comprise adjuvants, such as wetting agents, emulsifying suspending, sweetening, flavoring and perfuming agents.

As noted above 5-lipoxygenase products are involved in a number of inflammatory and allergic disease states and thus, the compounds of the present invention are useful in the treatment of such disease states. The treatment of psoriasis and other inflammatory and allergic dermatological disorders is a preferred embodiment of the invention.

The following examples illustrate the synthesis of starting materials and products of the present invention.

PREPARATION OF STARTING MATERIALS

Procedure 1

Preparation of 12-Phenyldodecanoic Acid via Cyclic Anhydride Route

A. 1,10-Decanedicarboxylic Anhydride

A stirred mixture of 23 gms (0.1 mole) of 1,10-decanedicarboxylic acid and 18 gms (0.1 mole) of acetic anhydride was refluxed for 18 hours and then concentrated in vacuo to remove acetic acid and excess acetic anhydride. The residue was dissolved in 300 ml methylene chloride, filtered, washed with ice-cold 5% sodium bicarbonate solution, water, and saturated sodium chloride. After the final separation of the layers the organic solution was dried over MgSO$_4$, filtered, and evaporated in vacuo to give 20 gms crude product. This was purified by dissolving it in 100 ml boiling methylene chloride, filtering hot, diluting with 200 ml hexanes, and refrigerating. This resulted 13 gms pure title product m.p. 85°–9°.

B. 11-Benzoylundecanoic Acid

To a stirred suspension of 18 gms AlCl$_3$ (0.135 mole) in 150 ml dry benzene was added 13 gms 1,10-decanedicarboxylic anhydride in small portions over 15 minutes, then the mixture was refluxed for 6 hours. The solid was filtered off, stirred for 2.5 hours in 350 ml 2N HCl, removed by filtration, and stirred in 300 ml 1N NaOH was then heated to 70° and filtered hot. As the solution cooled, solid material (sodium salt of the product) crystallized out. This salt was dissolved in hot water, acidified to pH 3 with concentrated HCl, filtered after cooling, and dried to give 5.5 gm of the desired 11-benzoylundecanoic acid m.p. 83°–6°.

C. 12-Phenyldodecanoic Acid

To a solution of 1 gm Hg$_2$Cl$_2$ in 30 ml H$_2$O was added 1 ml of concentrated HCl followed by 24 gms powdered Zn (portion wise) with mechanical stirring. The resulting mixture was stirred together for 5 minutes, then the liquid phase was decanted off, and 15 ml H$_2$O was added, followed by 36 ml concentrated HCl. This mixture was cooled to room temperature (the reaction to this point is exothermic), then 5.4 gms 11-benzoylundecanoic acid was added followed by 25 ml toluene. The resulting mixture was stirred and refluxed for 20 hours; 12 ml concentrated HCl was added during the first 6 hours of the reflux. The reaction mixture was cooled, the liquid was decanted, the phases were separated and the solid was three times triturated with 25 ml ether. The aqueous phase was 3×15 ml ether extracted; all organic phases were combined, washed with water and brine and dried over MgSO$_4$. The drying agent was filtered off, and the solvents were removed in vacuo to give a solid residue. This residue was dissolved in ether, extracted with dilute NaOH, and the organic layer was discarded. The aqueous layer was acidified with concentrated HCl, then extracted with there. This ether solution was washed with water and brine, dried over MgSO$_4$, filtered, and evaporated in vacuo to give 4.2 gms title product which was used without further purification.

Procedure 2

Preparation of 12-Benzoyldodecanoic Acid by Half-acid/Half-ester Route

A. Dimethyl 1,11-Undecanedicarboxylate

To a mixture of 6.5 gms 1,11-undecanedicarboxylic acid and 125 ml CH$_3$OH was added 1 ml concentrated H$_2$SO$_4$ and 5 gms 3A molecular sieves. This mixture was refluxed for 18 hours, cooled to room temperature, and then solid NaHCO$_3$ was added in small portions (foaming). The resulting mixture was filtered and evaporated in vacuo. The residue was dissolved in a mixture of 200 ml CH$_2$Cl$_2$ and 30 ml water. The mixture was shaken in a separatory funnel, the organic layer was separated, washed with 5% NaHCO$_3$ solution, water, then brine, dried over MgSO$_4$, filtered, and evaporated in vacuo to give 6.4 gms of low-melting solid which was used directly in the next step.

B. Monomethyl 1,11-Undecanedicarboxylate

To a stirred solution of 6.4 gms dimethyl 1,11-undecanedicarboxylate in 200 ml CH$_3$OH was added a solution of 1.3 gms KOH in 10 ml H$_2$O and the resulting mixture was stirred at room temperature overnight. the solvent was removed in vacuo and the residue was triturated with 100 ml H$_2$O. The water-insoluble material was dissolved in ether, determined to be starting material, and was recycled. The aqueous solution was made acidic to pH 3 and the precipitated solid filtered and dried to give 3.4 gms title product with m.p. 85°–90°. Another 1.6 gms was recovered from the recycled starting material.

C. 12-(Methoxycarbonyl)dodecanoyl Chloride

To a cold solution of 4.8 gms monomethyl 1,11-undecanedicarboxylate in 10 ml CH$_2$Cl$_2$ was added 5 ml SOCl$_2$ dropwise over 5 minutes; then it was stirred at room temperature for 18 hours. The solvent was removed in vacuo to give 4.8 gms of an oily residue which was used without further purification.

D. Methyl(12-Benzoyl)dodecanoate

To a stirred suspension of 3 gms AlCl$_3$ in 15 ml dry benzene at 40° was added the acid chloride from the previous step. The resulting mixture was refluxed for 2 hours, then cooled and poured over 200 ml ice containing 15 ml concentrated HCl. After stirring for 1½ hours the aqueous mixture was extracted 3×50 ml CH$_2$Cl$_2$. The organic phases were combined, washed with water, 5% NaHCO$_3$, brine, and dried over MgSO$_4$. The drying was filtered off and the solvent was removed in vacuo to give 4.5 gms yellow oil whose IR spectrum showed two C=O peaks plus the presence of aromatic C—H bonds. This oil was hydrolyzed directly in the next step.

E. 12-Benzoyldodecanoic Acid

A mixture of 4.5 gms crude ester from the previous step, 20 ml CH$_3$OH, and 30 ml of H$_2$O containing 2 gms NaOH was refluxed for 4 hours and cooled to room temperature. The solvent was removed in vacuo and triturated with a little cold water. The solid was filtered, washed with a little 1:1 ether:hexane mixture, and dissolved in hot water. The hot solution was acidified with concentrated HCl and the precipitate collected by filtration. The solid was purified by column chromatography in CH$_2$Cl$_2$ over 50 gms silica gel.

Ten fractions of 30 ml each were collected and discarded, then the eluting solvent was changed to 10% EtOAc/CH$_2$Cl$_2$ and the next 23 fractions were collected and combined, corresponding to the third major component. The solvents were removed in vacuo to give 0.7 gm yellow oil whose IR showed an acid O—H and two C=O stretching bonds between 1680–1720 cm$^{-1}$. The NMR showed the expected aromatic and aliphatic signals. This product was reduced as described above to give 13-phenyl-tridecanoic acid.

EXAMPLES

Example 1

Preparation of 9-Phenylnonanohydroxamic Acid

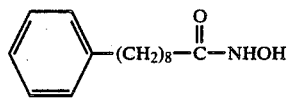

Into a 100 ml, 3 neck flask equipped with thermometer, drying tube, stirrer and dropping funnel is placed phenylnonanoic acid (10 gms, 0.0426 mole) and methylene chloride (20 ml). The resulting stirred mixture is cooled to 5° and thionyl chloride (6.2 gms, 0.052 mole) is added dropwise during 5 minutes, then stirred at room temperature for 18 hours. The methylene chloride and excess thionyl chloride are removed in vacuo to an oil, 10.8 gms (100%). This is diluted with methylene chloride (15 ml) and then added to a stirred mixture of hydroxylamine hydrochloride (3.6 gms, 0.052 mole), anhydrous sodium carbonate (5 gms, 0.052 mole) and methylene chloride (60 ml). During the addition, the temperature of the reaction is maintained between 5°–10° by regulating the addition. After stirring this mixture for ½ hour, water (6 ml) is added dropwise during 5 minutes, then the mixture is stirred at room temperature for 18 hours. The reaction mixture is diluted with methylene chloride (60 ml) and water (30 ml). The organic layer is separated and washed with water (2×30 ml), brine (2×30 ml), and dried over magnesium sulfate, then filtered and concentrated in vacuo to a solid residue. One recrystallization from methylene chloride (100 ml) gives 6.7 gms (63%) of pure title product, m.p. 75°–7°.

Example 2

Following the general procedure of Example 1, the following compounds were prepared from the appropriate phenylalkyl carboxylic acid starting materials:

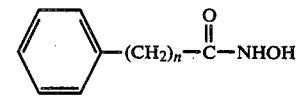

| Compound | n | m.p. | Elemental Analysis |
|---|---|---|---|
| 2a | 6 | 64–66° C. | |
| 2b | 7 | 79–81° C. | |
| 2c | 9 | 77–79° C. | |
| 2d | 10 | oil | * |
| 2e | 11 | 88–91° C. | |

-continued

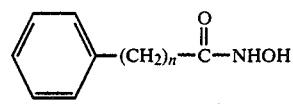

| Compound | n | m.p. | Elemental Analysis |
|---|---|---|---|
| *Calculated | C 73.60 | H 9.81 | N 5.05 |
| Found | C 73.30 | H 9.88 | N 4.44 |

We claim:

1. A compound of the formula

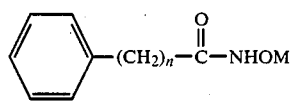

wherein n is an integer from six to eleven and M is hydrogen or a pharmaceutically acceptable cation.

2. A compound according to claim 1 wherein n is 7, 8 or 9.

3. A compound according to claim 1 wherein n=8.

4. The compound having the formula

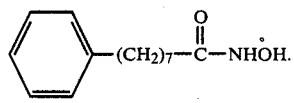

5. The compound having the formula

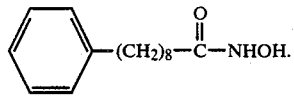

6. The compound having the formula

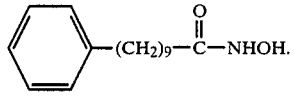

7. A method of inhibiting 5-lipoxygenase activity in a mammalian host in need of such treatment which comprises administering to said host an amount of a compound of the formula

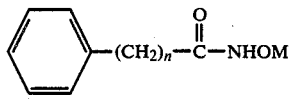

wherein n is an integer from six to eleven and M is hydrogen or a pharmaceutically acceptable cation in an amount effective to inhibit 5-lipoxygenase activity in the host.

8. The method of claim 7 wherein the compound administered as the formula

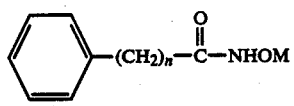

wherein n 7, 8 or 9 and M is hydrogen or a pharmaceutically acceptable cation.

9. The method of claim 7 wherein the compound administered has the formula

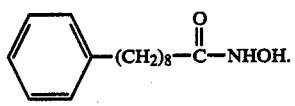

10. The method according to claim 7, 8 or 9 wherein the compound is administered topically.

11. A pharmaceutically composition in unit dosage form for the inhibition of 5-lipoxygenase activity in a mammalian host, comprising a 5-lipoxygenase-inhibiting effective amount of a compound of the formula

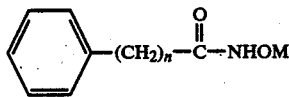

wherein n is an integer from six to eleven and M is hydrogen or a pharmaceutically acceptable cation and a pharmaceutically acceptable carrier.

12. A composition according to claim 11 wherein the active compound has the formula

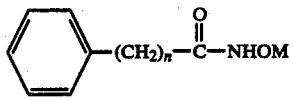

in which n is 7, 8 or 9 and M is hydrogen or a pharmaceutically acceptable cation.

13. A composition according to claim 11 wherein the active compound has the formula

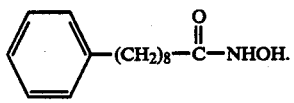

14. A method of preventing or treating inflammation in a mammalian host which comprises administering to a host in need of such treatment a therapeutically effective amount of a compound of the formula

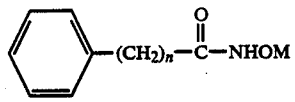

wherein n is an integer from six to eleven and M is hydrogen or a pharmaceutically acceptable cation 15. The method of claim 14 wherein the compound administered has the formula

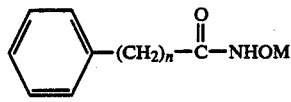

wherein n is 7, 8 or 9 and M is hydrogen or a pharmaceutically acceptable cation.

16. The method of claim 14 wherein the compound administered has the formula

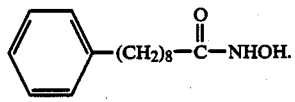

17. The method according to claim 14, 15 or 16 wherein the compound is administered topically.

18. A pharmaceutical composition for preventing or treating inflammation in mammals, which composition comprises a compound of the formula

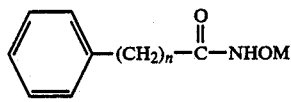

wherein n is an integer from six to eleven and M is hydrogen or a pharmaceutically acceptable cation in admixture with a pharmaceutically acceptable carrier.

19. The composition of claim 18 wherein the compound has the formula

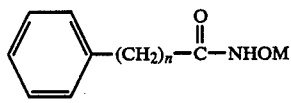

wherein n is 7, 8 or 9 and M is hydrogen or a pharmaceutically acceptable cation.

20. The composition of claim 18 wherein the compound has the formula

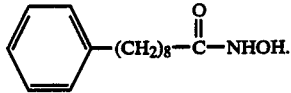

* * * * *